United States Patent
Breton et al.

(10) Patent No.: US 6,572,848 B1
(45) Date of Patent: Jun. 3, 2003

(54) USE OF A SUBSTANCE AGONIST OF A RECEPTOR ASSOCIATED WITH A CHLORINE OR POTASSIUM CANAL FOR TREATING SENSITIVE SKINS

(75) Inventors: Lionel Breton, Versailles (FR); Olivier De Lacharriere, Paris (FR); Isabelle Nonotte, Paris (FR)

(73) Assignee: Societe L'Oreal S.A., Paris (FR)

( * ) Notice: Subject to any disclaimer, the term of this patent is extended or adjusted under 35 U.S.C. 154(b) by 0 days.

(21) Appl. No.: 09/486,592

(22) PCT Filed: Aug. 27, 1998

(86) PCT No.: PCT/FR98/01861
§ 371 (c)(1),
(2), (4) Date: Apr. 28, 2000

(87) PCT Pub. No.: WO99/11238
PCT Pub. Date: Mar. 11, 1999

(30) Foreign Application Priority Data

Sep. 1, 1997 (FR) ............................................. 97 10853

(51) Int. Cl.[7] ................................................ A61K 7/48
(52) U.S. Cl. ............................... 424/78.02; 424/78.05; 424/78.07; 424/401; 514/221; 514/275; 514/302; 514/353; 514/354; 514/355; 514/356; 514/561; 514/711; 514/861; 514/863; 514/864; 514/887; 514/937; 514/944
(58) Field of Search ................................ 424/45, 78.05, 424/401, 78.02, 78.07; 514/887, 861, 863, 864, 937, 944, 221, 275, 302, 353, 354, 356, 561, 711

(56) References Cited

FOREIGN PATENT DOCUMENTS

| | | |
|---|---|---|
| DE | 43 28 871 | 3/1995 |
| EP | 0 312 700 | 4/1989 |
| EP | 0 463 190 | 1/1992 |
| EP | 0 514 553 | 11/1992 |
| EP | 0 704 210 | 4/1996 |
| FR | 2 273 514 | 1/1976 |
| WO | 91 18608 | 12/1991 |
| WO | 92 13518 | 8/1992 |

OTHER PUBLICATIONS

Patent Abstracts of Japan, vol. 096, No. 012 (C, Dec. 26, 1996 & JP 08217695 A (Pola Chem Ind). Aug. 27, 1996, see abstract.

Database WPI, Section Ch, Week 9807, Derwent Publications Ltd., London, GB: Class B04, AN 98–075248, XP002065464 & RU 2 080 854 C (Samsonov), Jun. 10, 1997, see abstract.

Patent Abstracts of Japan, vol. 12, No. 410 (C–540), 3257, & JP 63 150209 A (Kanebo) see abstract, 1988.

Michel Schorderet et al, *Pharmacologie: De Concepts Fondamentaux aux Applications Therapeutiques*, Editions Slatkine, Geneva, Switzerland (1992), pp. 121–122, 341–344 (with English translation).

Cardozo et al, *J. Neurophysiol.*, 74(3), 1137–1148 (1995), abstract only.

Greif et al, *J. Neurophysiol.*, 83(2), 1010–8 (2000), abstract only.

*Primary Examiner*—S. Mark Clardy
(74) *Attorney, Agent, or Firm*—Burns, Doane, Swecker & Mathis, L.L.P.

(57) ABSTRACT

Agonists of chlorine/potassium channel receptor, for example taurine, gamma-aminobutyric acid (GABA), isoguvacin, isonipecotic acid, 4,5,6,7-tetrahydroisoxazolo-(5,4-c)pyrid-3(2H)-one, a benzodiazepine, steroids, and cromakalim, pinacidil, nicorandil and minoxidil, are well suited for treating sensitive human skin and are especially useful for treating/eliminating skin itching, pruritus, tautness, tingling and/or erythema.

80 Claims, No Drawings

USE OF A SUBSTANCE AGONIST OF A RECEPTOR ASSOCIATED WITH A CHLORINE OR POTASSIUM CANAL FOR TREATING SENSITIVE SKINS

This application has been filed under 35 USC 371 as the national stage of international application PCT/FR98/01861, filed Aug. 27, 1998.

BACKGROUND OF THE INVENTION

1. Technical Field of the Invention

The present invention relates to the use of a substance which is an agonist of a receptor associated with a chlorine channel or with a potassium channel, except for amino acids and derivatives thereof, in a cosmetic and/or dermatological composition, for treating sensitive skin, including the scalp, and mucous membranes, of human beings. The invention also relates to a process for treating sensitive skin.

2. Description of the Prior Art

It is known that certain skin types are more sensitive than others. The symptoms of sensitive skin were hitherto poorly characterized and the problem of these skin types was consequently poorly defined; no-one knew exactly what process was involved in skin sensitivity. Some thought that sensitive skin was skin which reacted to cosmetic products, while others thought that it was skin which reacted to several external factors, not necessarily associated with cosmetic products.

Certain tests have been developed in an attempt to define sensitive skin, for example tests with lactic acid and with DMSO (dimethyl sulphoxide) which are known to be irritant substances: see for example the article by K. Lammintausta et al., Dermatoses, 1988, 36, pages 45–49; and the article by T. Agner and J. Serup, Clinical and Experimental Dermatology, 1989, 14, pages 214–217. However, these tests did not make it possible to correctly characterize sensitive skin.

Moreover, sensitive skin was likened to allergic skin.

Since the characteristics of sensitive skin were not well known, it was hitherto very difficult to treat such skin types, and they were treated indirectly, for example by limiting the use of products of irritant nature, such as surfactants, preserving agents or fragrances, in cosmetic compositions.

The Applicant has carried out many clinical tests and has been able to determine the symptoms associated with sensitive skin. These symptoms are, in particular, subjective signs, which are essentially dysaesthetic sensations. The term dysaesthetic sensations is understood to refer to the more or less painful sensations experienced in a region of skin, such as stinging, tingling, itching or pruritus, burning, heating, discomfort, tautness, etc. The Applicant has also been able to show that sensitive skin was not allergic skin (see in this respect patent FR-A-2 719 474).

Document WO 91/18608 describes the use of triazolobenzodiazepines as PAF (Platelet-Activating Factor) antagonists for treating pruritus. The Applicant has thus found that sensitive skin can be divided into two major clinical forms: irritable and/or reactive skin, and intolerant skin.

Irritable and/or reactive skin is skin which reacts by pruritus, i.e. by itching or stinging, to various factors such as the environment, emotions, foods, the wind, rubbing, shaving, soap, surfactants, hard water with a high calcium concentration, temperature variations or wool. In general, these signs are associated with dry skin with or without dry patches, or with skin which displays erythema.

Intolerant skin is skin which reacts, by sensations of heating, tautness, tingling and/or redness, to various factors such as the environment, emotions and foods. In general, these signs are associated with hyperseborrhoeic or acneic skin with or without dry patches, and with erythema.

"Sensitive" scalps have a more univocal clinical semeiology: the sensations of pruritus and/or of stinging and/or heating are essentially triggered by local factors such as rubbing, soap, surfactants, hard water with a high calcium concentration, shampoos or lotions. These sensations are also sometimes triggered by factors such as the environment, emotions and/or foods. Erythema and hyperseborrhoea of the scalp and the presence of dandruff are often associated with the above signs.

Moreover, in certain anatomical regions such as the major folds (groin, genital, axillary, popliteal, anal and submammary regions and in the crook of the elbow) and the feet, sensitive skin is reflected in pruriginous sensations and/or dysaesthetic sensations (heating, stinging) associated in particular with sweat, rubbing, wool, surfactants, hard water with a high calcium concentration and/or temperature variations.

To determine whether or not a skin is sensitive, the Applicant has also developed tests, in particular with capsaicin and triethanolamine.

SUMMARY OF THE INVENTION

The Applicant has now discovered that sensitive skin is associated with a modification in the skin's nerve excitability. Consequently, the use of agonists of the receptors associated with the chlorine and/or potassium channels present in skin tissue can make it possible to obtain a preventive and/or curative effect on sensitive skin.

Specifically, the cell membranes of each nerve fibre comprise many ion channels, and in particular chlorine or potassium channels. The role of these various channels is to allow the chloride and potassium ions to pass from both sides of the nerve cell membrane, these ion exchanges (influx of negatively charged chlorides and exit of positively charged potassium) leading to electrical changes which make the sensitive nerve fibres less excitable (this phenomenon is known as membrane hyperpolarization). The neuronal receptors associated with the chlorine or potassium channels are, in particular for the chlorine channels, glycine receptors (glycine-strychnine sensitive receptors) and GABA receptors ($GABA_A$ receptors).

Moreover, it is known that, in the central nervous system, it is possible to reduce the cellular excitability with various pharmacological agents which have an effect on the glycine-strychnine sensitive receptors or on the $GABA_A$ receptors associated with the chlorine channels of the central nervous system (see W. Sieghart, Trends in Pharmacological Science, December 1992, vol. 131, pages 446 to 450). Furthermore, it is also possible to reduce the cellular excitability with various pharmacological agents which have an effect on the potassium channels (see S. D. Longman, Medicinal Research Reviews, 1992, vol. 12, page 73).

After numerous clinical tests, the Applicant has found that skin tissue comprises receptors associated with the chlorine or potassium channels, which had not been envisaged hitherto, and that a link exists between the chlorine or potassium channels of sensitive nerve fibres of the cutaneous peripheral nervous system and sensitive skin. The Applicant has thus found that it is possible to act on these channels to treat sensitive skin.

No-one had hitherto established a link between the chlorine or potassium channels of the sensitive nerve fibres of the cutaneous peripheral nervous system and sensitive skin, and no-one had found that sensitive skin could be treated by acting on the chlorine or potassium channels by activating the receptors in or in the region of these channels. Substances which can activate the chlorine or potassium channel receptors, and thus lead to the influx of chloride or potassium ions into the cells, are known as agonist substances.

Thus, the present invention relates to the use of at least one substance which is an agonist of at least one receptor associated with at least one chlorine or potassium channel, present in skin tissue, except for amino acids and derivatives thereof and triazolobenzodiazepines, in and/or for the manufacture of a topical cosmetic or dermatological composition for treating sensitive skin.

The subject of the invention is also the use of at least one substance which is an agonist of at least one receptor associated with at least one chlorine or potassium channel, present in skin tissue, except for amino acids and derivatives thereof and triazolobenzodiazepines, in and/or for the manufacture of a topical cosmetic or dermatological composition for treating, or even eliminating, itching, pruritus, tingling, heating, tautness, stinging and/or erythema.

The invention also relates to the use of at least one substance which is an agonist of at least one receptor associated with at least one chlorine or potassium channel of at least one cutaneous afferent nerve, except for amino acids and derivatives thereof and triazolobenzodiazepines, in and/or for the manufacture of a topical cosmetic or dermatological composition for treating sensitive skin.

The invention also relates to the use of at least one substance which is an agonist of at least one receptor associated with at least one chlorine or potassium channel of at least one cutaneous afferent nerve, except for amino acids and derivatives thereof and triazolobenzodiazepines, in and/or for the manufacture of a topical cosmetic and/or dermatological composition for treating, or even eliminating, itching, pruritus, tingling, heating, tautness, stinging and/or erythema.

A subject of the invention is also a process for the cosmetic treatment of sensitive skin, which consists in applying topically, to the skin of an individual with sensitive skin, a cosmetic topical composition containing at least one substance which is an agonist of at least one receptor associated with at least one chlorine or potassium channel, present in skin tissue, except for amino acids and derivatives thereof and triazolobenzodiazepines.

DETAILED DESCRIPTION OF BEST MODE AND SPECIFIC/PREFERRED EMBODIMENTS OF THE INVENTION

Several receptors associated with the chlorine or potassium channel exist. They are, in particular, the glycine-strychnine sensitive receptors and the $GABA_A$ receptors, the latter receptors themselves comprising several subunits consisting of the GABA site, the benzodiazepine site and a steroid-type site. Any substance acting as an agonist of these receptors or sites can be used for treating sensitive skin in accordance with the invention.

In order for a substance to be acknowledged as an agonist of the chlorine or potassium channel receptors, it must satisfy at least one of the following characteristics:

it must show a muscle-relaxant effect in a functional test on isolated organ; and/or it must show activity of chlorine- or potassium-channel-opening type by electrophysiological measurement, optionally by means of binding to at least one of the various receptors associated with the chlorine or potassium channel.

As agonist substances which can be used in the invention to activate the glycine-strychnine sensitive receptors associated with the chlorine channels, mention may be made of taurine.

As agonist substances which can be used in the invention to activate the $GABA_A$ receptors associated with the chlorine channels, mention may be made of gamma-aminobutyric acid (GABA); isoguvacin; isonipecotic acid; 4,5,6,7-tetrahydroisoxazolo(5,4-c)pyrid-3(2H)-one (THIP); benzodiazepines such as nitrazepam (1,3-dihydro-7-nitro-5-phenyl-2H-1,4-benzodiazepin-2-one), diazepam (7-chloro-1,3-dihydro-1-methyl-5-phenyl-2H-1,4-benzodiazepin-2-one), flunitrazepam (5-(2-fluorophenyl)-1,3-dihydro-1-methyl-7-nitro-2H-1,4-benzodiazepin-2-one) and oxazepam (7-chloro-1,3-dihydro-3-hydroxy-5-phenyl-2H-1,4-benzodiazepin-2-one); certain steroids such as alfaxalone (3-hydroxypregnane-11,20-dione).

As substances which are agonists of the receptors associated with the potassium channels, which can be used in the invention, mention may be made of minoxidil, pinacidil, nicorandil and cromakalim.

In the compositions according to the invention, the agonist of a receptor associated with the chlorine or potassium channel is preferably used in an amount ranging from 0.00001 to 20% by weight relative to the total weight of the composition, and in particular in an amount ranging from 0.001 to 10% by weight relative to the total weight of the composition.

The compositions according to the invention can be in any pharmaceutical form normally used for topical application.

The amounts of the various constituents in the compositions according to the invention are those conventionally used in the fields considered and are suitable for their pharmaceutical form.

The topical-application compositions of the invention comprise a medium which is compatible with the skin, including the scalp, and mucous membranes such as the lips. These compositions can be in particular in the form of aqueous, alcoholic or aqueous-alcoholic solutions, gels, water-in-oil or oil-in-water emulsions having the appearance of a cream or a gel, microemulsions or aerosols, or alternatively in the form of vesicular dispersions containing ionic and/or nonionic lipids. These pharmaceutical forms are prepared according to the usual methods of the fields considered.

These topical-application compositions can in particular constitute a cosmetic or dermatological protective, treatment or care composition for the face, the neck, the hands or the body (for example a day cream, a night cream, an antisun cream or oil, or a body milk), a make-up composition (for example a foundation) or an artificial tanning composition.

When the composition of the invention is an emulsion, the proportion of fatty substances it contains can range from 5% to 80% by weight, and preferably from 5% to 50% by weight, relative to the total weight of the composition. The fatty substances and emulsifiers used in the composition in emulsion form are chosen from those used conventionally in the cosmetics or dermatological field.

As fatty substances which can be used in the invention, mention may be made of oils of mineral origin (petroleum jelly), oils of plant origin (liquid fraction of karite butter) and hydrogenated derivatives thereof, oils of animal origin, synthetic oils (perhydrosqualene), silicone oils (polydimethylsiloxane) and fluoro oils. Other fatty substances which may also be mentioned are fatty alcohols (cetyl alcohol and stearyl alcohol), fatty acids (stearic acid) and waxes.

The emulsifiers can be present in the composition in a proportion ranging from 0.3 to 30% by weight, and preferably from 0.5 to 30% by weight, relative to the total weight of the composition.

In a known manner, the cosmetic or dermatological compositions of the invention can also contain additives that are common in the corresponding fields, such as hydrophilic or lipophilic gelling agents, preserving agents, antioxidants, solvents, fragrances, fillers, screening agents and dyestuffs. Moreover, these compositions can contain hydrophilic or lipophilic active agents. The amount of these various additives or active agents are those conventionally used in the cosmetics or dermatological field, and, for example, from 0.01 to 20% of the total weight of the composition. Depending on their nature, these additives or active agents can be introduced into the fatty phase, into the aqueous phase and/or into the lipid vesicles.

The examples which follow are given for illustrative purposes in order to provide a better understanding of the invention. The amounts indicated are percentages by weight.

EXAMPLE 1

Facial Care Lotion

| | |
|---|---|
| Taurine | 8% |
| Antioxidant | 0.05% |
| Preserving agent | 0.3% |
| Ethanol (solvent) | 8% |
| Water | qs 100% |

The lotion obtained acts on sensitive skin when used repeatedly (applied twice a day for one month).

EXAMPLE 2

Facial Care Gel

| | |
|---|---|
| Minoxidil | 0.5% |
| Hydroxypropylcellulose (Klucel H sold by the company Hercules) (gelling agent) | 1% |
| Perserving agent | 0.3% |
| Antioxidant | 0.05% |
| Water | qs 100% |

The gel obtained can be applied daily morning and evening for one month.

EXAMPLE 3

Facial Care Cream (Oil-in-water emulsion)

| | |
|---|---|
| Flunitrazepam | 0.1% |
| Glyceryl stearate (emulsifier) | 2% |
| Polysorbate 60 (Tween 60 sold by the company ICI) (emulsifier) | 1% |
| Stearic acid | 1.4% |
| Triethanolamine (neutralizer) | 0.7% |
| Carbomer (Carbopol 940 sold by the company Goodrich) | 0.4% |
| Liquid fraction of karite butter | 12% |

| -continued | |
|---|---|
| Perhydrosqualene | 12% |
| Preserving agent | 0.3% |
| Fragrance | 0.5% |
| Antioxidant | 0.05% |
| Water | qs 100% |

A rich white cream is obtained, which acts on sensitive skin and which can be applied daily.

EXAMPLE 4

Facial Care Cream (Oil-in-water Emulsion)

| | |
|---|---|
| Flunitrazepam | 0.2% |
| Glyceryl mono- and distearate | 2% |
| Cetyl alcohol | 1.5% |
| Cetylstearyl alcohol/33 EO oxyethylenated cetylstearyl alcohol mixture | 7% |
| Polydimethylsiloxane | 1.5% |
| Liquid petroleum jelly | 17.5% |
| Preserving agent | 0.3% |
| Fragrance | 0.5% |
| Glycerol | 12.5% |
| Water | qs 100% |

What is claimed is:

1. A cosmetic or dermatological method for treating capsaicin- or triethanolamine-sensitive skin in an individual in need of such treatment, said method comprising topically applying to said capsaicin- or triethanolamine-sensitive skin, in an amount effective to treat such skin, at least one substance which is an agonist of at least one receptor associated with at least one chlorine or potassium channel present in skin tissue, said substance being other than an amino acid or a triazolobenzodiazepine.

2. A cosmetic or dermatological method according to claim 1, wherein said capsaicin- or triethanolamine-sensitive skin exhibits at least one symptom selected from the group consisting of itching, pruritus, tingling, heating, tautness, stinging and erythema.

3. A cosmetic or dermatological method according to claim 1, wherein said substance is applied in the form of a topical cosmetic or dermatological composition in which said substance is present in an amount ranging from 0.00001 to 20% by weight relative to the total weight of the composition.

4. A cosmetic or dermatological method according to claim 3, wherein said substance is present in the composition in an amount ranging from 0.001 to 10% by weight relative to the total weight of the composition.

5. A cosmetic or dermatological method according to claim 1, wherein said substance is applied in the form of a topical cosmetic or dermatological composition which is an aqueous, alcoholic or aqueous-alcoholic solution, a gel, a water-in-oil or oil-in-water emulsion having the appearance of a cream or a gel, a microemulsion, an aerosol or a vesicular dispersion.

6. A cosmetic or dermatological method according to claim 5, wherein said substance is present in the composition in an amount ranging from 0.001 to 10% by weight relative to the total weight of the composition.

7. A cosmetic or dermatological method for treating capsaicin- or triethanolamine-sensitive skin in an individual in need of such treatment, said method comprising topically applying to said capsaicin- or triethanolamine-sensitive skin, in an amount effective to treat such skin, at least one substance which is an agonist of at least one receptor associated with at least one chlorine or potassium channel of at least one cutaneous afferent nerve, said substance being other than an amino acid or a triazolobenzodiazepine.

8. A cosmetic or dermatological method according to claim 7, wherein said capsaicin- or triethanolamine-sensitive skin exhibits at least one symptom selected from the group consisting of itching, pruritus, tingling, beating, tautness, stinging and erythema.

9. A cosmetic or dermatological method according to claim 7, wherein said substance is applied in the form of a topical cosmetic or dermatological composition in which said substance is present in an amount ranging from 0.00001 to 20% by weight relative to the total weight of the composition.

10. A cosmetic or dermatological method according to claim 9, wherein said substance is present in the composition in an amount ranging from 0.001 to 10% by weight relative to the total weight of the composition.

11. A cosmetic or dermatological method according to claim 7, wherein said substance is applied in the form of a topical cosmetic or dermatological composition which is an aqueous, alcoholic or aqueous-alcoholic solution, a gel, a water-in-oil or oil-in-water emulsion having the appearance of a cream or a gel, a microemulsion, an aerosol or a vesicular dispersion.

12. A cosmetic or dermatological method according to claim 11, wherein said substance is present in the composition in an amount ranging from 0.001 to 10% by weight relative to the total weight of the composition.

13. A cosmetic or dermatological method for treating irritable, reactive or intolerant skin in an individual in need of such treatment, said method comprising topically applying to said irritable, reactive or intolerant skin, in an amount effective to treat such skin, at least one substance which is an agonist of at least one receptor associated with at least one chlorine or potassium channel present in skin tissue, said substance being other than an amino acid or a triazolobenzodiazepine.

14. A cosmetic or dermatological method according to claim 13, wherein said substance is applied in the form of a topical cosmetic or dermatological composition in which said substance is present in an amount ranging from 0.00001 to 20% by weight relative to the total weight of the composition.

15. A cosmetic or dermatological method according to claim 14, wherein said substance is present in the composition in an amount ranging from 0.001 to 10% by weight relative to the total weight of the composition.

16. A cosmetic or dermatological method according to claim 13, wherein said substance is applied in the form of a topical cosmetic or dermatological composition which is an aqueous, alcoholic or aqueous-alcoholic solution, a gel, a water-in-oil or oil-in-water emulsion having the appearance of a cream or a gel, a microemulsion, an aerosol or a vesicular dispersion.

17. A cosmetic or dermatological method according to claim 16, wherein said substance is present in the composition in an amount ranging from 0.001 to 10% by weight relative to the total weight of the composition.

18. A cosmetic or dermatological method for treating irritable, reactive or intolerant skin in an individual in need of such treatment, said method comprising topically applying to said irritable, reactive or intolerant skin, in an amount effective to treat such skin, at least one substance which is an agonist of at least one receptor associated with at least one chlorine or potassium channel of at least one cutaneous afferent nerve, said substance being other than an amino acid or a triazolobenzodiazepine.

19. A cosmetic or dermatological method according to claim 18, wherein said substance is applied in the form of a topical cosmetic or dermatological composition in which said substance is present in an amount ranging from 0.00001 to 20% by weight relative to the total weight of the composition.

20. A cosmetic or dermatological method according to claim 19, wherein said substance is present in the composition in an amount ranging from 0.001 to 10% by weight relative to the total weight of the composition.

21. A cosmetic or dermatological method according to claim 18, wherein said substance is applied in the form of a topical cosmetic or dermatological composition which is an aqueous, alcoholic or aqueous-alcoholic solution, a gel, a water-in-oil or oil-in-water emulsion having the appearance of a cream or a gel, a microemulsion, an aerosol or a vesicular dispersion.

22. A cosmetic or dermatological method according to claim 21, wherein said substance is present in the composition in an amount ranging from 0.001 to 10% by weight relative to the total weight of the composition.

23. A cosmetic or dermatological method for treating capsaicin- or triethanolamine-sensitive skin in an individual in need of such treatment, said method comprising topically applying to said capsaicin- or triethanolamine-sensitive skin, in an amount effective to treat such skin, at least one substance which is an agonist of at least one receptor associated with at least one chlorine or potassium channel present in skin tissue, said substance being selected from the group consisting of taurine, gamma-aminobutyric acid, isoguvacin, isonipecotic acid, 4,5,6,7-tetrahydroisoxazolo (5,4-c)pyrid-3(2H)-one, a steroid, nicorandil, pinacidil, minoxidil, cromakalim and a benzodiazepine other than a triazolobenzodiazepine.

24. A cosmetic or dermatological method according to claim 23, wherein said capsaicin- or triethanolamine-sensitive skin exhibits at least one symptom selected from the group consisting of itching, pruritus, tingling, heating, tautness, stinging and erythema.

25. A cosmetic or dermatological method according to claim 23, wherein said substance is selected from the group consisting of taurine, gamma-aminobutyric acid, isoguvacin, isonipecotic acid, 4,5,6,7-tetrahydroisoxazolo (5,4-c)pyrid-3(2H)-one, alfaxalone, nicorandil, pinacidil, minoxidil, cromakalim, nitrazepam, diazepam, flunitrazepam and oxazepam.

26. A cosmetic or dermatological method according to claim 25, wherein said capsaicin- or triethanolamine-sensitive skin exhibits at least one symptom selected from the group consisting of itching, pruritus, tingling, heating, tautness, stinging and erythema.

27. A cosmetic or dermatological method according to claim 23, wherein said substance is applied in the form of a topical cosmetic or dermatological composition in which said substance is present in an amount ranging from 0.00001 to 20% by weight relative to the total weight of the composition.

28. A cosmetic or dermatological method according to claim 27, wherein said substance is present in the composition in an amount ranging from 0.001 to 10% by weight relative to the total weight of the composition.

29. A cosmetic or dermatological method according to claim 23, wherein said substance is applied in the form of a topical cosmetic or dermatological composition which is an aqueous, alcoholic or aqueous-alcoholic solution, a gel, a water-in-oil or oil-in-water emulsion having the appearance of a cream or a gel, a microemulsion, an aerosol or a vesicular dispersion.

30. A cosmetic or dermatological method according to claim 29, wherein said substance is present in the composition in an amount ranging from 0.001 to 10% by weight relative to the total weight of the composition.

31. A cosmetic or dermatological method for treating capsaicin- or triethanolamine-sensitive skin in an individual in need of such treatment, said method comprising topically applying to said capsaicin- or triethanolamine-sensitive skin, in an amount effective to treat such skin, at least one substance which is an agonist of at least one receptor associated with at least one chlorine or potassium channel of at least one cutaneous afferent nerve, said substance being selected from the group consisting of taurine, gamma-aminobutyric acid, isoguvacin, isonipecotic acid, 4,5,6,7-tetrahydroisoxazolo(5,4-c)pyrid-3(2H)-one, a steroid, nicorandil, pinacidil, minoxidil, cromakalim and a benzodiazepine other than a triazolobenzodiazepine.

32. A cosmetic or dermatological method according to claim 31, wherein said capsaicin- or triethanolamine-sensitive skin exhibits at least one symptom selected from the group consisting of itching, pruritus, tingling, heating, tautness, stinging and erythema.

33. A cosmetic or dermatological method according to claim 31, wherein said substance is selected from the group consisting of taurine, gamma-aminobutyric acid, isoguvacin, isonipecotic acid, 4,5,6,7-tetrahydroisoxazolo(5,4-c)pyrid-3(2H)-one, alfaxalone, nicorandil, pinacidil, minoxidil, cromakalim, nitrazepam, diazepam, flunitrazepam and oxazepam.

34. A cosmetic or dermatological method according to claim 33, wherein said capsaicin- or triethanolamine-sensitive skin exhibits at least one symptom selected from the group consisting of itching, pruritus, tingling, heating, tautness, stinging and erythema.

35. A cosmetic or dermatological method according to claim 31, wherein said substance is applied in the form of a topical cosmetic or dermatological composition in which said substance is present in an amount ranging from 0.00001 to 20% by weight relative to the total weight of the composition.

36. A cosmetic or dermatological method according to claim 35, wherein said substance is present in the composition in an amount ranging from 0.001 to 10% by weight relative to the total weight of the composition.

37. A cosmetic or dermatological method according to claim 31, wherein said substance is applied in the form of a topical cosmetic or dermatological composition which is an aqueous, alcoholic or aqueous-alcoholic solution, a gel, a water-in-oil or oil-in-water emulsion having the appearance of a cream or a gel, a microemulsion, an aerosol or a vesicular dispersion.

38. A cosmetic or dermatological method according to claim 37, wherein said substance is present in the composition in an amount ranging from 0.001 to 10% by weight relative to the total weight of the composition.

39. A cosmetic or dermatological method for treating irritable, reactive or intolerant skin in an individual in need of such treatment, said method comprising topically applying to said irritable, reactive or intolerant skin, in an amount effective to treat such skin, at least one substance which is an agonist of at least one receptor associated with at least one chlorine or potassium channel present in sensitive skin, said substance being selected from the group consisting of taurine, gamma-aminobutyric acid, isoguvacin, isonipecotic acid, 4,5,6,7-tetrahydroisoxazolo(5,4-c)pyrid-3(2H)-one, a steroid, nicorandil, pinacidil, minoxidil, cromakalim and a benzodiazepine other than a triazolobenzodiazepine.

40. A cosmetic or dermatological method according to claim 39, wherein said substance is selected from the group consisting of taurine, gamma-aminobutyric acid, isoguvacin, isonipecotic acid, 4,5,6,7-tetrahydroisoxazolo(5,4-c)pyrid-3(2H)-one, alfaxalone, nicorandil, pinacidil, minoxidil, cromakalim, nitrazepam, diazepam, flunitrazepam and oxazepam.

41. A cosmetic or dermatological method according to claim 39, wherein said substance is applied in the form of a topical cosmetic or dermatological composition in which said substance is present in an amount ranging from 0.00001 to 20% by weight relative to the total weight of the composition.

42. A cosmetic or dermatological method according to claim 41, wherein said substance is present in the composition in an amount ranging from 0.001 to 10% by weight relative to the total weight of the composition.

43. A cosmetic or dermatological method according to claim 39, wherein said substance is applied in the form of a topical cosmetic or dermatological composition which is an aqueous, alcoholic or aqueous-alcoholic solution, a gel, a water-in-oil or oil-in-water emulsion having the appearance of a cream or a gel, a microemulsion, an aerosol or a vesicular dispersion.

44. A cosmetic or dermatological method according to claim 43, wherein said substance is present in the composition in an amount ranging from 0.001 to 10% by weight relative to the total weight of the composition.

45. A cosmetic or dermatological method for treating irritable, reactive or intolerant skin in an individual in need of such treatment, said method comprising topically applying to said irritable, reactive or intolerant skin, in an amount effective to treat such skin, at least one substance which is an agonist of at least one receptor associated with at least one chlorine or potassium channel of at least one cutaneous afferent nerve, said substance being selected from the group consisting of taurine, gamma-aminobutyric acid, isoguvacin, isonipecotic acid, 4,5,6,7-tetrahydroisoxazolo(5,4-c)pyrid-3(2H)-one, a steroid, nicorandil, pinacidil, minoxidil, cromakalim and a benzodiazepine other than a triazolobenzodiazepine.

46. A cosmetic or dermatological method according to claim 45, wherein said substance is selected from the group consisting of taurine, gamma-aminobutyric acid, isoguvacin, isonipecotic acid, 4,5,6,7-tetrahydroisoxazolo(5,4-c)pyrid-3(2H)-one, alfaxalone, nicorandil, pinacidil, minoxidil, cromakalim, nitrazepam, diazepam, flunitrazepam and oxazepam.

47. A cosmetic or dermatological method according to claim 45, wherein said substance is applied in the form of a topical cosmetic or dermatological composition in which said substance is present in an amount ranging from 0.00001 to 20% by weight relative to the total weight of the composition.

48. A cosmetic or dermatological method according to claim 47, wherein said substance is present in the composition in an amount ranging from 0.001 to 10% by weight relative to the total weight of the composition.

49. A cosmetic or dermatological method according to claim 45, wherein said substance is applied in the form of a topical cosmetic or dermatological composition which is an aqueous, alcoholic or aqueous-alcoholic solution, a gel, a water-in-oil or oil-in-water emulsion having the appearance of a cream or a gel, a microemulsion, an aerosol or a vesicular dispersion.

50. A cosmetic or dermatological method according to claim 49, wherein said substance is present in the composition in an amount ranging from 0.001 to 10% by weight relative to the total weight of the composition.

51. A cosmetic or dermatological method for treating itching, pruritus, tingling, heating, tautness, stinging or erythema of the skin in an individual in need of such treatment, said method comprising topically applying to the skin of said individual, in an amount effective to treat such itching, pruritus, tingling, heating, tautness, stinging or erythema, at least one substance which is an agonist of at least one receptor associated with at least one chlorine or potassium channel present in skin tissue, said substance being other than an amino acid or a triazolobenzodiazepine.

52. A cosmetic or dermatological method according to claim 51, wherein said substance is applied in the form of a topical cosmetic or dermatological composition in which said substance is present in an amount ranging from 0.00001 to 20% by weight relative to the total weight of the composition.

53. A cosmetic or dermatological method according to claim 52, wherein said substance is present in the composition in an amount ranging from 0.001 to 10% by weight relative to the total weight of the composition.

54. A cosmetic or dermatological method according to claim 51, wherein said substance is applied in the form of a topical cosmetic or dermatological composition which is an aqueous, alcoholic or aqueous-alcoholic solution, a gel, a water-in-oil or oil-in-water emulsion having the appearance of a cream or a gel, a microemulsion, an aerosol or a vesicular dispersion.

55. A cosmetic or dermatological method according to claim 54, wherein said substance is present in the composition in an amount ranging from 0.001 to 10% by weight relative to the total weight of the composition.

56. A cosmetic or dermatological method for treating itching, pruritus, tingling, heating, tautness, stinging or erythema of the skin in an individual in need of such treatment, said method comprising topically applying to the skin of said individual, in an amount effective to treat such itching, pruritus, tingling, heating, tautness, stinging or erythema, at least one substance which is an agonist of at least one receptor associated with at least one chlorine or potassium channel of at least one cutaneous afferent nerve, said substance being other than an amino acid or a triazolobenzodiazepine.

57. A cosmetic or dermatological method according to claim 56, wherein said substance is applied in the form of a topical cosmetic or dermatological composition in which said substance is present in an amount ranging from 0.00001 to 20% by weight relative to the total weight of the composition.

58. A cosmetic or dermatological method according to claim 57, wherein said substance is present in the composition in an amount ranging from 0.001 to 10% by weight relative to the total weight of the composition.

59. A cosmetic or dermatological method according to claim 56, wherein said substance is applied in the form of a topical cosmetic or dermatological composition which is an aqueous, alcoholic or aqueous-alcoholic solution, a gel, a water-in-oil or oil-in-water emulsion having the appearance of a cream or a gel, a microemulsion, an aerosol or a vesicular dispersion.

60. A cosmetic or dermatological method according to claim 59, wherein said substance is present in the composition in an amount ranging from 0.001 to 10% by weight relative to the total weight of the composition.

61. A cosmetic or dermatological method for treating itching, pruritus, tingling, heating, tautness, stinging or erythema of the skin in an individual in need of such treatment, said method comprising topically applying to the skin of said individual, in an amount effective to treat such itching, pruritus, tingling, heating, tautness, stinging or erythema, at least one substance which is an agonist of at least one receptor associated with at least one chlorine or potassium channel present in skin tissue, said substance being selected from the group consisting of taurine, gamma-aminobutyric acid, isoguvacin, isonipecotic acid, 4,5,6,7-tetrahydroisoxazolo(5,4-c)pyrid-3(2H)-one, a steroid, nicorandil, pinacidil, minoxidil, cromakalim and a benzodiazepine other than a triazolobenzodiazepine.

62. A cosmetic or dermatological method according to claim 61, wherein said substance is selected from the group consisting of taurine, gamma-aminobutyric acid, isoguvacin, isonipecotic acid, 4,5,6,7-tetrahydroisoxazolo (5,4-c)pyrid-3(2H)-one, alfaxalone, nicorandil, pinacidil, minoxidil, cromakalim, nitrazepam, diazepam, flunitrazepam and oxazepam.

63. A cosmetic or dermatological method according to claim 62, wherein said substance is applied in the form of a topical cosmetic or dermatological composition in which said substance is present in an amount ranging from 0.00001 to 20% by weight relative to the total weight of the composition.

64. A cosmetic or dermatological method according to claim 63, wherein said substance is present in the composition in an amount ranging from 0.001 to 10% by weight relative to the total weight of the composition.

65. A cosmetic or dermatological method according to claim 62, wherein said substance is applied in the form of a topical cosmetic or dermatological composition which is an aqueous, alcoholic or aqueous-alcoholic solution, a gel, a water-in-oil or oil-in-water emulsion having the appearance of a cream or a gel, a microemulsion, an aerosol or a vesicular dispersion.

66. A cosmetic or dermatological method according to claim 65, wherein said substance is present in the composition in an amount ranging from 0.001 to 10% by weight relative to the total weight of the composition.

67. A cosmetic or dermatological method according to claim 61, wherein said substance is applied in the form of a topical cosmetic or dermatological composition in which said substance is present in an amount ranging from 0.00001 to 20% by weight relative to the total weight of the composition.

68. A cosmetic or dermatological method according to claim 67, wherein said substance is present in the composition in an amount ranging from 0.001 to 10% by weight relative to the total weight of the composition.

69. A cosmetic or dermatological method according to claim 61, wherein said substance is applied in the form of a topical cosmetic or dermatological composition which is an aqueous, alcoholic or aqueous-alcoholic solution, a gel, a water-in-oil or oil-in-water emulsion having the appearance of a cream or a gel, a microemulsion, an aerosol or a vesicular dispersion.

70. A cosmetic or dermatological method according to claim 69, wherein said substance is present in the composition in an amount ranging from 0.001 to 10% by weight relative to the total weight of the composition.

71. A cosmetic or dermatological method for treating itching, pruritus, tingling, heating, tautness, stinging or erythema of the skin in an individual in need of such treatment, said method comprising topically applying to the skin of said individual, in an amount effective to treat such itching, pruritus, tingling, heating, tautness, stinging or erythema, at least one substance which is an agonist of at least one receptor associated with at least one chlorine or potassium channel of at least one cutaneous afferent nerve, said substance being selected from the group consisting of taurine, gamma-aminobutyric acid, isoguvacin, isonipecotic acid, 4,5,6,7-tetrahydroisoxazolo(5,4-c)pyrid-3(2H)-one, a steroid, nicorandil, pinacidil, minoxidil, cromakalim and a benzodiazepine other than a triazolobenzodiazepine.

72. A cosmetic or dermatological method according to claim 71, wherein said substance is selected from the group consisting of taurine, gamma-aminobutyric acid, isoguvacin, isonipecotic acid, 4,5,6,7-tetrahydroisoxazolo (5,4-c)pyrid-3(2H)-one, alfaxalone, nicorandil, pinacidil, minoxidil, cromakalim, nitrazepam, diazepam, flunitrazepam and oxazepam.

73. A cosmetic or dermatological method according to claim 72, wherein said substance is applied in the form of a topical cosmetic or dermatological composition in which said substance is present in an amount ranging from 0.00001 to 20% by weight relative to the total weight of the composition.

74. A cosmetic or dermatological method according to claim 73, wherein said substance is present in the composition in an amount ranging from 0.001 to 10% by weight relative to the total weight of the composition.

75. A cosmetic or dermatological method according to claim 72, wherein said substance is applied in the form of a topical cosmetic or dermatological composition which is an aqueous, alcoholic or aqueous-alcoholic solution, a gel, a water-in-oil or oil-in-water emulsion having the appearance of a cream or a gel, a microemulsion, an aerosol or a vesicular dispersion.

76. A cosmetic or dermatological method according to claim 75, wherein said substance is present in the composition in an amount ranging from 0.001 to 10% by weight relative to the total weight of the composition.

77. A cosmetic or dermatological method according to claim 71, wherein said substance is applied in the form of a topical cosmetic or dermatological composition in which said substance is present in an amount ranging from 0.00001 to 20% by weight relative to the total weight of the composition.

78. A cosmetic or dermatological method according to claim 77, wherein said substance is present in the composition in an amount ranging from 0.001 to 10% by weight relative to the total weight of the composition.

79. A cosmetic or dermatological method according to claim 71, wherein said substance is applied in the form of a topical cosmetic or dermatological composition which is an aqueous, alcoholic or aqueous-alcoholic solution, a gel, a water-in-oil or oil-in-water emulsion having the appearance of a cream or a gel, a microemulsion, an aerosol or a vesicular dispersion.

80. A cosmetic or dermatological method according to claim 79, wherein said substance is present in the composition in an amount ranging from 0.001 to 10% by weight relative to the total weight of the composition.

* * * * *